US012597486B2

(12) United States Patent
Choi et al.

(10) Patent No.: US 12,597,486 B2
(45) Date of Patent: Apr. 7, 2026

(54) DISEASE PREDICTION METHOD, APPARATUS, AND COMPUTER PROGRAM

(71) Applicant: ONCOCROSS CO., LTD., Seoul (KR)

(72) Inventors: Jin Woo Choi, Gyeonggi-do (KR); Yi Rang Kim, Sejong (KR)

(73) Assignee: ONCOCROSS CO., LTD., Seoul (KR)

( * ) Notice: Subject to any disclaimer, the term of this patent is extended or adjusted under 35 U.S.C. 154(b) by 955 days.

(21) Appl. No.: 17/789,342

(22) PCT Filed: Dec. 14, 2020

(86) PCT No.: PCT/KR2020/018236
§ 371 (c)(1),
(2) Date: Jun. 27, 2022

(87) PCT Pub. No.: WO2021/137471
PCT Pub. Date: Jul. 8, 2021

(65) Prior Publication Data
US 2023/0042132 A1     Feb. 9, 2023

(30) Foreign Application Priority Data

Jan. 2, 2020     (KR) ........................ 10-2020-0000506
Sep. 21, 2020     (KR) ........................ 10-2020-0121316

(51) Int. Cl.
G06N 3/08          (2023.01)
G06N 5/022          (2023.01)
(Continued)

(52) U.S. Cl.
CPC .............. G16B 20/00 (2019.02); G06N 3/08 (2013.01); G06N 5/022 (2013.01); G16B 40/20 (2019.02); G16H 10/40 (2018.01); G16H 50/50 (2018.01)

(58) Field of Classification Search
CPC ........ G16B 20/00; G16B 40/20; G16B 25/10; G06N 3/08; G06N 5/022; G06N 3/0464;
(Continued)

(56) References Cited

U.S. PATENT DOCUMENTS

| 5,862,304 A | * | 1/1999 | Ravdin | .................. | G06N 3/065 |
| | | | | | 706/924 |
| 2005/0032066 A1 | * | 2/2005 | Heng | ..................... | G16H 50/50 |
| | | | | | 702/20 |

(Continued)

FOREIGN PATENT DOCUMENTS

| KR | 10-1884609 B1 | 8/2018 | | |
| KR | 101884609 | * | 8/2018 | ............. A61B 5/055 |

(Continued)

OTHER PUBLICATIONS

Dolezal et al.; Diagnostic and prognostic implications of ribosomal protein transcript expression patterns in human cancers; Mar. 12, 2018; Open access; vol. 18; pp. 1-14 (Year: 2018).*

(Continued)

*Primary Examiner* — Phenuel S Salomon
(74) *Attorney, Agent, or Firm* — Harness, Dickey & Pierce, P.L.C.

(57) ABSTRACT

A disease prediction method, apparatus, and computer program are provided. A disease prediction method according to several embodiments of the present disclosure can comprise the steps of: constructing a disease prediction model by learning learning data including ribosome data and disease information for learning, acquiring test ribosome data of an examinee; and predicting disease information about the examinee form the test ribosome data by using the disease prediction model. The disease prediction model can accurately predict disease information about the examinee by detecting and learning the characteristics of ribosome data, which vary according to disease information.

12 Claims, 14 Drawing Sheets

(51) Int. Cl.

| | | |
|---|---|---|
| *G16B 20/00* | (2019.01) | |
| *G16B 40/20* | (2019.01) | |
| *G16H 10/40* | (2018.01) | |
| *G16H 50/50* | (2018.01) | |

(58) Field of Classification Search
CPC ........ G16H 10/40; G16H 50/50; G16H 30/40; G16H 50/70; G16H 50/20
See application file for complete search history.

(56)               References Cited

U.S. PATENT DOCUMENTS

| | | | |
|---|---|---|---|
| 2016/0228003 A1* | 8/2016 | Apte ..................... | A61B 5/0022 |
| 2017/0308981 A1* | 10/2017 | Razavian ............... | G16H 40/60 |
| 2018/0070825 A1 | 3/2018 | Apte et al. | |
| 2019/0172587 A1* | 6/2019 | Park .......................... | G06N 3/09 |
| 2021/0057107 A1* | 2/2021 | Solomon .............. | G06N 3/0455 |
| 2021/0104321 A1* | 4/2021 | Lipsky ................... | G16H 20/10 |

FOREIGN PATENT DOCUMENTS

| | | |
|---|---|---|
| KR | 10-2019-0021471 A | 3/2019 |
| WO | WO-2006/052218 A1 | 5/2006 |

OTHER PUBLICATIONS

International Search Report from corresponding PCT Application No. PCT/KR2020/018236, dated Mar. 24, 2021.
Dolezal, J. M., et al.; "Diagnostic and prognostic implications of ribosomal protein transcript expression pattern in human cancers", BMC cancer, 2018, vol. 18, document 275, pp. 1-14.

* cited by examiner

DISEASE PREDICTION METHOD, APPARATUS, AND COMPUTER PROGRAM

CROSS-REFERENCE TO RELATED APPLICATIONS

This application is a national phase application of PCT Application No. PCT/KR2020/018236, filed on Dec. 14, 2020, which claims priority to Korean Patent Application Nos. 10-2020-0000506, filed on Jan. 2, 2020 and 10-2020-0121316, filed on Sep. 21, 2020. The entire disclosure of the applications identified in this paragraph is incorporated herein by reference.

TECHNICAL FIELD

The present disclosure relates to a disease prediction method, apparatus, and computer program. More specifically, the present disclosure relates to a method for predicting disease information such as the presence, type, and prognosis of a disease from ribosome data of an examinee using a machine-learning model, an apparatus for performing the method, and a computer program in which the method is implemented.

BACKGROUND ART

By using computational methods and bio-informatics, researchers may find new uses of existing compounds or predict the uses of new compounds. This approach is widely used in the discovery of new drugs.

The discovery and development of new drugs always takes a lot of time and money and goes through a complex process. Accordingly, in recent years, research has been actively carried out to combine disciplines from various fields such as bio-informatics, chemi-informatics, computer science, and computer-aided drug discovery/design (CADD) to reduce the time required for the discovery and development of new drugs and to enhance the effects of new drugs.

However, since the prior art employs a rule-based approach, it is impossible to predict a situation in which a rule may not be defined beyond human recognition.

SUMMARY

The technical object to be achieved through some embodiments of the present disclosure is to provide a method for predicting disease information such as the presence, type, and prognosis of a disease from ribosome data of an examinee using a machine-learning model, an apparatus for performing the method, and a computer program in which the method is implemented.

Technical objects of the present disclosure are not limited to those described above, and other technical objects not mentioned above may also be clearly understood from the descriptions given below by those skilled in the art to which the present disclosure belongs.

To achieve the technical object above, a method for predicting disease according to some embodiments of the present disclosure comprises, as a method for predicting disease of an examinee in a computing device, constructing a disease prediction model by learning ribosome data for training and training data including disease information, acquiring ribosome test data of the examinee, and predicting disease information of the examinee from the ribosome test data by using the disease prediction model, wherein the ribosome data for training and the ribosome test data may include data related to expression rates of ribosomal proteins.

In some embodiments, the ribosome data for training may further include protein expression rates between a large sub-unit and a small sub-unit and data on ribosomal proteins with an expression level above a threshold and ribosomal proteins with an expression level below the threshold.

In some embodiments, the training data may further include an image of a target tissue, and the disease prediction model may include a first neural network receiving the image of a target tissue and outputting a first output value related to the disease information, a second neural network receiving the ribosome data for training and outputting a second output value related to the disease information, and a third neural network predicting disease information on the target tissue by receiving the first output value and the second output value, wherein the first neural network may be composed of convolutional neural networks.

In some embodiments, the disease prediction model may include a first neural network receiving data in the form of an image related to the ribosomal proteins and outputting a first output value related to the disease information, a second neural network receiving the ribosome data for training and outputting a second output value related to the disease information, and a third neural network predicting disease information by receiving the first output value and the second output value, wherein the first neural network may be composed of convolutional neural networks.

In some embodiments, the disease information may include information on an overall survival period and a relapse-free survival period of a diseased person; the disease prediction model may include a first neural network receiving the ribosome data for training and outputting an output value related to the disease information, a second neural network receiving the output value and predicting the overall survival period, and a third neural network predicting the relapse-free survival period by receiving the output value; and the constructing the disease prediction model training the first neural network and the second neural network using the ribosome data for training and the information on the overall survival period and training the first neural network and the third neural network using the ribosome data for training and the information on the relapse-free survival period.

In some embodiments, the constructing the disease prediction model may include detecting an expression pattern of ribosomal proteins associated with the disease information by comparing the ribosomal protein expression rate of a normal person with the ribosomal protein expression rate of a diseased person, assigning sample weights to data samples constituting the training data using the detected expression pattern, and learning the training data based on the sample weights.

In some embodiments, the constructing the disease prediction model may include: constructing a temporary disease prediction model by learning the training data; generating second ribosome data samples by changing at least a portion of expression rates of ribosomal proteins from first ribosome data samples constituting the ribosome data for training; acquiring a first prediction value by entering the first ribosome data samples to the temporary disease prediction model and acquiring a second prediction value by entering the second ribosome data samples to the temporary disease prediction model; detecting an expression pattern of ribosomal proteins associated with the disease information based on a difference between the first prediction value and the second prediction value; assigning sample weights to data samples constituting the training data using the detected expression pattern; and constructing the disease prediction model by re-learning the training data based on the sample weights.

To solve the technical problem above, a disease prediction apparatus according to some embodiments of the present disclosure may comprise a memory storing one or more instructions and a processor performing, by executing the stored one or more instructions, an operation of constructing a disease prediction model by learning ribosome data for training and training data including disease information, an operation of acquiring ribosome test data of an examinee, and an operation of predicting disease information of the examinee from the ribosome test data using the disease prediction model, wherein the ribosome data for training and the ribosome test data may include data related to expression rates of ribosomal proteins.

To solve the technical problem above, a computer program according to some embodiments of the present disclosure, by being combined with a computing device, may be stored in a computer-readable recording medium for executing: constructing a disease prediction model by learning ribosome data for training and training data including disease information, acquiring ribosome test data of an examinee, and predicting disease information of the examinee from the ribosome test data using the disease prediction model. At this time, the ribosome data for training and the ribosome test data may include data related to expression rates of ribosomal proteins.

Advantageous Effects

According to some embodiments of the present disclosure, a disease prediction model may be constructed by machine learning of ribosome data and disease information, and disease information may be predicted from the ribosome data of an examinee through the constructed disease prediction model. By detecting and learning the relationship between ribosome data and disease information that is difficult for humans to accurately identify (i.e., detecting and learning features of ribosome data that depends on disease information), the disease prediction model may accurately predict disease information such as the presence, type, and prognosis of disease from the examinee's ribosome data.

Also, in addition to the expression rates of the ribosomal proteins, a disease prediction model may be learned using various ribosome data such as the expression rate between subunits that make up the ribosome and the type of low-expressed or overexpressed ribosomal proteins. In this case, since the disease prediction model predicts disease information by considering the expression level of the ribosomal proteins from various aspects, the prediction accuracy of the disease prediction model may be further improved.

Also, a disease prediction model may be learned further using data on disease-related features that appear in tissue images, the expression level according to the location of a ribosomal protein, the location relationship between ribosomal proteins, and the like. Accordingly, the prediction accuracy of the disease prediction model may be further improved.

Also, an expression pattern of ribosomal proteins associated with disease information may be detected, and weighted learning may be performed on ribosome data samples including the detected expression patterns. In this case, since the disease prediction model better learns the expression characteristics of the ribosomal proteins associated with the disease information, the prediction accuracy of the disease prediction model may be further improved.

The advantageous effects due to the technical principles of the present disclosure are not limited to those described above, and other effects not mentioned above may be clearly understood from the descriptions given below by those skilled in the art to which the present disclosure belongs.

BRIEF DESCRIPTION OF THE DRAWINGS

FIG. 4 illustrates an exemplary method for constructing a disease prediction model according to some embodiments of the present disclosure.

FIGS. 7, 8 and 9 are exemplary diagrams illustrating the detailed structure and learning method of a disease prediction model according to a third embodiment of the present disclosure.

DESCRIPTION OF EXEMPLARY EMBODIMENTS

In what follows, preferred embodiments of the present disclosure will be described in detail with reference to appended drawings. The advantages and features of the present disclosure, and a method for achieving them will be clearly understood with reference to the embodiments described in detail together with appended drawings. However, the technical principles and spirit of the present disclosure are not limited to the embodiments disclosed below but may be implemented in various other forms; rather, the present embodiments are provided to make the present disclosure complete and inform those skilled in the art clearly of the technical scope of the present disclosure, and the technical principles and spirit of the present disclosure may be defined within the technical scope of the appended claims.

In assigning reference symbols to the constituting elements of each drawing, it should be noted that the same constituting elements are intended to have the same symbol as much as possible, even if they are shown on different drawings. Also, in describing the present disclosure, if it is determined that a detailed description of a related well-known configuration or function incorporated herein unnecessarily obscure the gist of the present disclosure, the detailed description thereof will be omitted.

Unless otherwise defined, all terms (including technical and scientific terms) used herein may be used in a sense commonly understood by those skilled in the art to which the present disclosure belongs. Also, terms defined in commonly used dictionaries are not ideally or excessively interpreted unless otherwise explicitly defined. The terms used herein are intended to describe embodiments and are not intended to limit the present disclosure. In the present disclosure, a singular expression includes a plural expression unless clearly indicated otherwise in the corresponding phrase.

Also, in describing the constituting elements of the present disclosure, terms such as first, second, A, B, (a), and (b) may be used. Such terms are intended only to distinguish one constituting element from the others and do not limit the nature, sequence, or order of the constituting elements. If a constituting element is said to be "linked to," "combined with," or "connected to" a different constituting element, it should be understood that the constituting element is linked or connected to the different constituting element, but another constituting element may be "linked," "combined," or "connected" between the two constituting elements.

The term "comprises" and/or "comprising" used in the present disclosure indicates the existence of a constituting element, a step, an operation, and/or a component described but does not exclude the existence or addition of one or more other constituting elements, steps, operations, and/or components.

In what follows, various embodiments of the present disclosure will be described in detail with reference to appended drawings.

Figure 1:
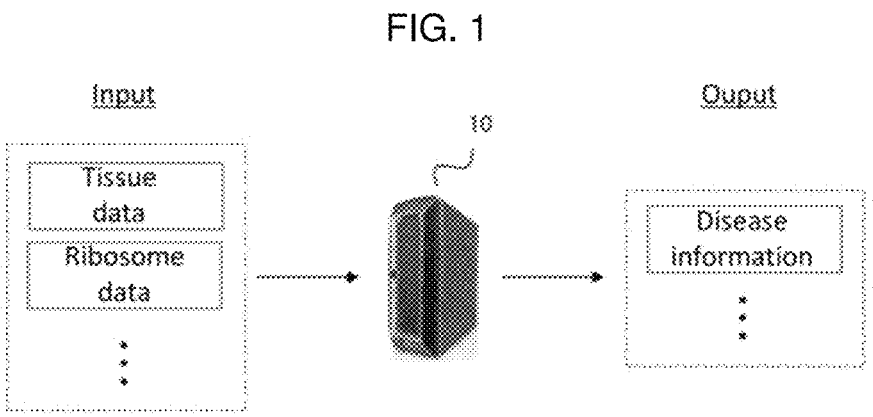
FIG. 1 illustrates an apparatus for predicting disease and input and output data according to some embodiments of the present disclosure.

FIG. 1 illustrates an apparatus 10 for predicting disease and input and output data according to some embodiments of the present disclosure.

As shown in FIG. 1, the apparatus 10 for predicting disease may be a computing device that predicts and outputs disease information based on input data such as tissue data and ribosome data. Here, the computing device may be, but is not limited to, a notebook, desktop, or laptop computer and may include all kinds of devices equipped with computing capabilities. For an example of the computing device, refer to FIG. 14. In what follows, for the convenience of descriptions, the "apparatus 10 for predicting disease" is abbreviated to a "prediction device 10."

More specifically, the prediction device 10 constructs a disease prediction model through machine-learning of the illustrated input/output data and predict the disease information of an examinee from the examinee's data (e.g., tissue data or ribosome data) through the constructed disease prediction model.

A disease prediction model may be implemented, for example, based on a neural network model. However, the technical scope of the present disclosure is not limited thereto, and the disease prediction model may be implemented based on a classic machine learning models such as decision trees, support vector machines, or logistic regression. Also, the neural network model may include various types of neural networks including artificial neural networks (ANNs), convolutional neural networks (CNNs), recurrent neural networks (RNNs), or a combination thereof. Hereinafter, for the convenience of descriptions, the "disease prediction model" is abbreviated to a "predictive model."

The disease information corresponds to a prediction target of the prediction model, which may include, for example, the presence or absence, type (category), progression stage, prognosis (e.g., an overall survival period, a relapse-free survival period, and goodness or badness of the prognosis) of disease and information processed from the above. However, the disease information is not limited thereto. For example, if a model that predicts the presence or absence of disease is to be constructed from ribosome data, the prediction model may be constructed based on learning of the ribosome data (i.e., learning the ribosome data of a normal and diseased person) by assigning a class label to the information on the presence or absence of the disease. Here, learning may mean updating the weights of the model (i.e., weight parameters) in such a way to minimize errors (e.g., the difference between a prediction value of the model calculated by a loss function and the ground-truth).

Next, the ribosome data may include the expression rate, expression location, expression distribution of the ribosomal protein; the expression rate of proteins between a large sub unit (LSU) and a small sub unit (SSU) that make up the ribosome; the type/number of ribosomal proteins in which the expression level (or expression rate) is above (or below a threshold); the protein type or protein expression rate around a particular site (e.g., E, P, or A site); and data processed from the above. However, the ribosome data are not limited thereto.

It should be noted that the expression rates of ribosomal proteins may mean the expression level of ribosomal proteins that make up the ribosome. Since those skilled in the art should be fully informed of the types of ribosomal proteins, descriptions related thereto will be omitted.

The reason for using ribosome data to predict disease information may be understood from the fact that the expression rates of ribosomal proteins vary between a normal and diseased person. Although it is difficult to determine the exact cause, if an expression pattern of the ribosomal proteins associated with the disease information may be learned (detected) through machine learning, the examinee's disease information may be more accurately and effectively predicted than from other methods.

Next, the tissue data may include a tissue type, a tissue-related image, lesion information, and data obtained by processing them. However, tissue data are not limited thereto.

A specific method by the prediction device 10 for constructing a prediction model and predicting the disease information of an examinee using the constructed prediction model will be described in detail later with reference to FIG. 2 and subsequent figures.

Meanwhile, although FIG. 1 shows an example in which the prediction device 10 is implemented by one computing device, the prediction device 10 may be implemented by a plurality of computing devices. In this case, a first function of the prediction device 10 may be implemented in a first computing device, and a second function may be implemented in a second computing device. Alternatively, a specific function of the prediction device 10 may be implemented in a plurality of computing devices.

Figure 2:
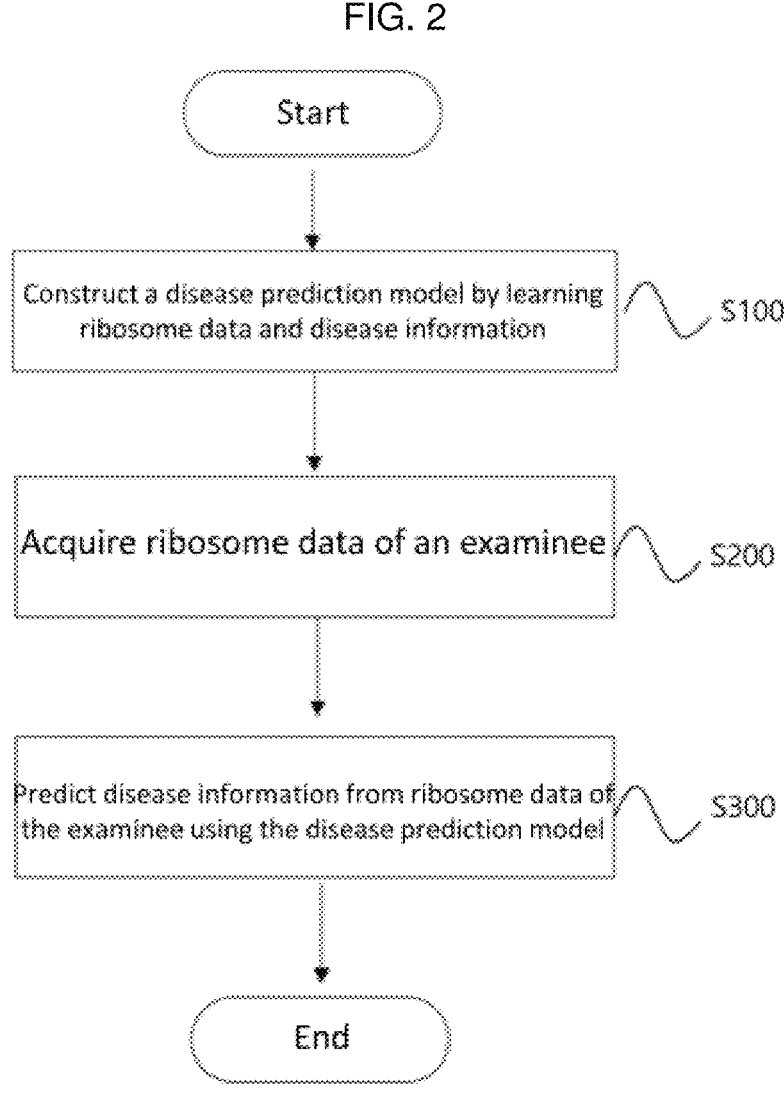
FIG. 2 is a flow diagram illustrating a method for predicting disease according to some embodiments of the present disclosure.
Figure 3:
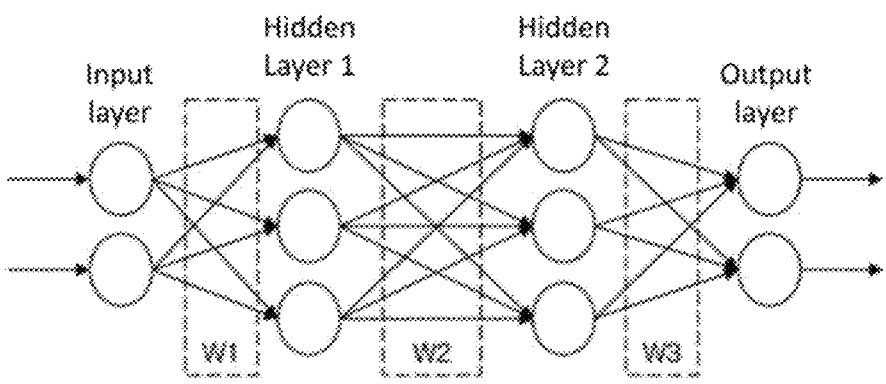
FIG. 3 illustrates the structure of an artificial neural network that may be referenced in some embodiments of the present disclosure.

So far, a prediction device 10 according to some embodiments of the present disclosure has been described briefly with reference to FIGS. 1 to 3. In what follows, a method for predicting disease according to some embodiments of the present disclosure will be described with reference to FIG. 2 and subsequent figures.

A computing device may perform each step of a method for predicting disease to be described below. In other words, each step of the method may be implemented using one or more instructions executed by a processor of the computing device. All the steps included in the method may be executed by one physical computing device but may be executed by being distributed over a plurality of physical computing devices. For example, a first computing device may perform first steps of the method, and a second computing device may perform second steps of the method. In what follows, descriptions will be given based on the assumption that each step of the method is performed by the prediction device 10 illustrated in FIG. 1. Therefore, if a subject is omitted for each operation in the following description, it may be understood that the operation is performed by the illustrated apparatus 10.

FIG. 2 is a flow diagram illustrating a method for predicting disease according to some embodiments of the present disclosure. However, the flow diagram is only a preferred embodiment for achieving the object of the present disclosure, and it should be understood that some steps may be added or deleted depending on the needs.

As shown in FIG. 2, the method for predicting disease may start at step S100 of constructing a prediction model by learning ribosome data and disease information. In other words, the training data of the prediction model may consist of ribosome data and disease information. However, the training data may further include tissue data in some other embodiments. The ribosome data may be named ribosome data for training to distinguish the data from the ribosome data of an examinee.

As mentioned above, the prediction model is a machine learning model, which may be, for example, a model implemented based on a neural network. As a more specific example, the prediction model may be a model based on an artificial neural network, as illustrated in FIG. 3. However, the technical scope of the present disclosure is not limited thereto. As shown in the figure, the artificial neural network model may consist of an input layer, hidden layers, and an output layer, and since those skilled in the art may clearly understand the function, operating principle, and a training method of each layer (e.g., a method of updating the weights of each layer in such a way to minimize errors through error backpropagation), descriptions thereof will be omitted.

Figure 4:
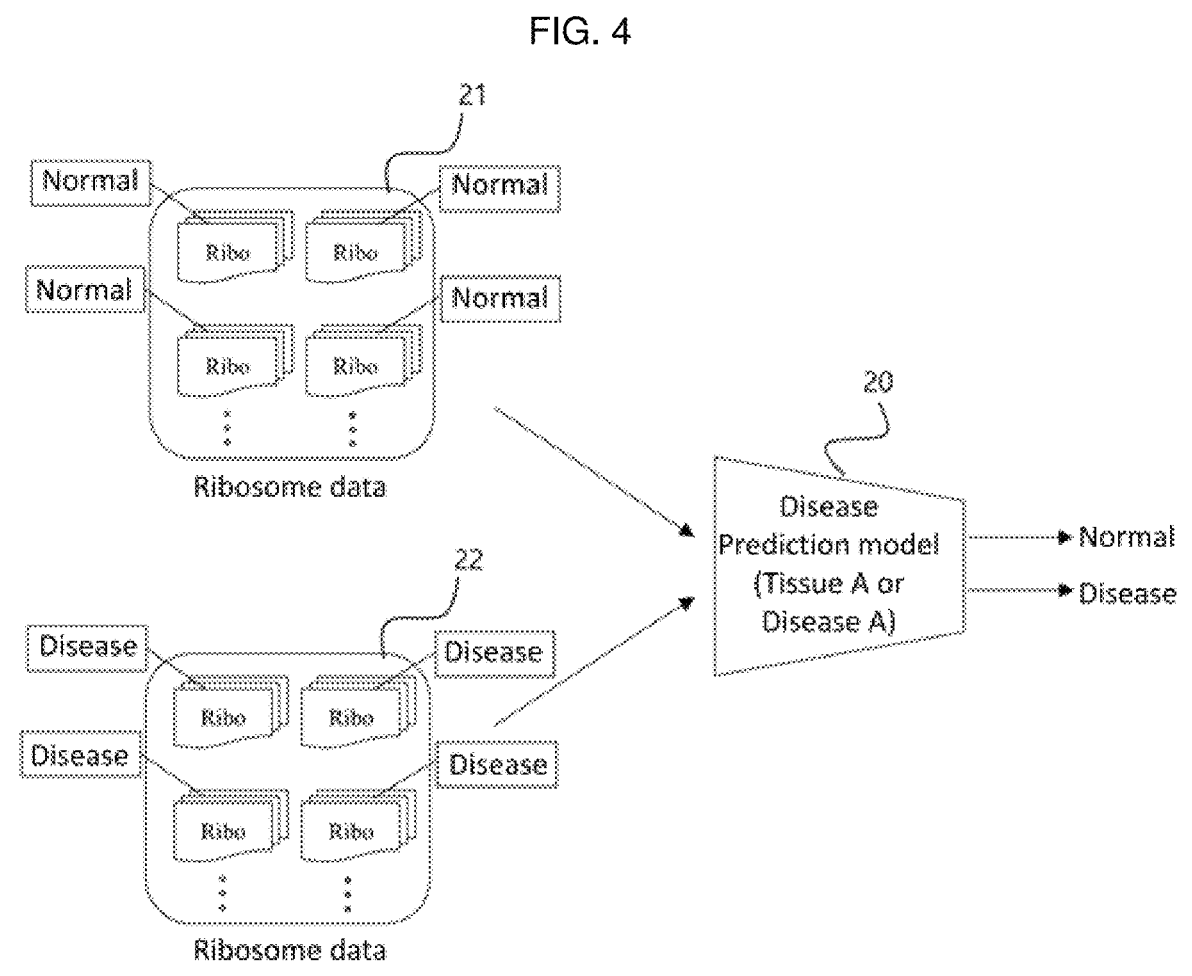

In the present step, the prediction model may be constructed for each tissue (or for each disease). In other words, a first prediction model for predicting disease information on a first tissue may be constructed, and a second prediction model for predicting disease information on a second tissue may be constructed separately from the first prediction model. For example, suppose a model that predicts the presence or absence (or type) of a disease (e.g., malignant tumor) in a particular tissue is constructed from ribosome data. In this case, as shown in FIG. 4, by learning a normal person's ribosome data 21 and a diseased person's ribosome data 21 for a particular tissue A, a model 20 that predicts the presence or absence of a disease in the particular tissue A may be constructed from the given ribosome data. Although FIG. 4 shows an example of constructing a model 20 that performs binary classification for the convenience of understanding, the technical scope of the present disclosure is not limited thereto. Depending on the design of the class labels, the prediction model may perform multiple classifications.

Alternatively, the prediction model may be constructed for each tissue and disease.

Alternatively, the prediction model may be constructed to predict disease information for a plurality of tissues. For example, when data about a plurality of tissues (e.g., types of tissues) and ribosome data are learned with disease information, a model for predicting disease information for the plurality of tissues may be constructed.

Meanwhile, the detailed structure of the prediction model and learning methods based on the structure may be designed in various ways, which may vary depending on the embodiments. The design variations will be described in detail later with reference to FIG. 5 and subsequent figures.

In the S200 step, the ribosome data of an examinee may be obtained. If the prediction model uses tissue data as input data, the examinee's tissue data may also be obtained in the present step. The ribosome data may be named ribosome data for inspection to distinguish the data from ribosome data for training.

In the S300 step, the disease information of the examinee may be predicted from the examinee's ribosome data using the prediction model. For example, if the prediction model predicts the presence or absence of a disease, whether the examinee is diseased may be predicted based on a prediction value (e.g., a confidence score for a normal or disease class) obtained by entering the examinee's ribosome data into the prediction model. As another example, if the prediction model predicts the prognosis of a disease (e.g., an overall survival period, a relapse-free survival period, and goodness or badness of the prognosis) (see FIG. 10), the prognosis of the examinee may be predicted based on the predicted value obtained by entering the examinee's ribosome data into the prediction model.

So far, with reference to FIGS. 2 to 4, a method for predicting disease according to some embodiments of the present disclosure has been described. In what follows, various embodiments related to the detailed structure of the prediction model and a learning method based thereon will be described with reference to FIG. 5 and subsequent figures. In addition, for the convenience of understanding, descriptions will be continued based on the assumption that the prediction model predicts the presence or absence of a disease (except for FIG. 10). However, the technical scope of the present disclosure is not limited thereto, and depending on the definition and design method of class labels, the prediction target of the prediction model may vary accordingly.

Figure 5:
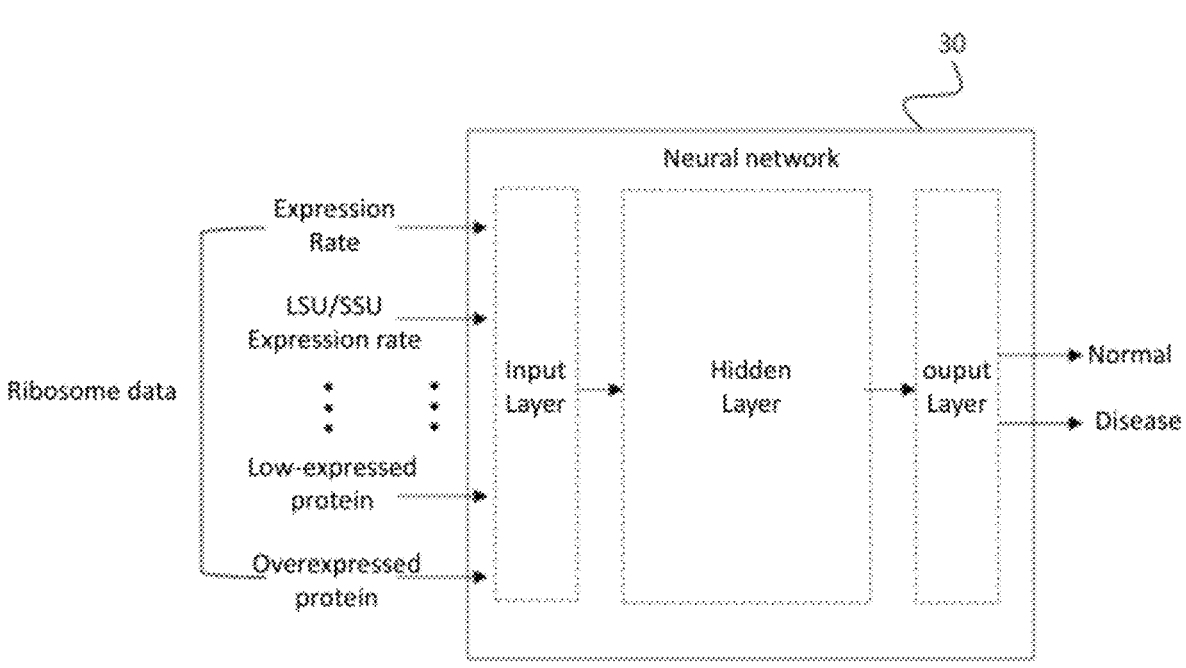
FIG. 5 is an exemplary diagram illustrating the detailed structure and learning method of a disease prediction model according to a first embodiment of the present disclosure.

FIG. 5 is an exemplary diagram illustrating the detailed structure and learning method of a disease prediction model according to a first embodiment of the present disclosure.

As shown in FIG. 5, the prediction model according to the first embodiment may be configured to include one or more neural networks 30. The neural network 30 may be an artificial neural network but, in some cases, may consist of different kinds of neural networks.

The neural network 30 may be trained to receive various ribosome data and output prediction values regarding disease information. For example, if the neural network 30 receives ribosome data and outputs a prediction value regarding the presence or absence of a disease, training may be performed by backpropagating errors between output prediction values and the ground truth values (i.e., the correct answers in the disease information) and updating weights of the neural network 30. The neural network 30 so trained as above may accurately predict the presence or absence of a disease from the examinee's ribosome data.

In the present embodiment, the ribosome data may include not only the expression rates of ribosomal proteins but also the expression rates of proteins between a large subunit (LSU) and a small sub unit (SSU); the type/number of ribosomal proteins in which the expression level (or expression rate) is above (or below a threshold) (i.e., low-expressed or overexpressed ribosomal proteins); and the protein type or protein expression rate around a particular site (e.g., E, P, A site). In this case, since the neural network

30 (or prediction model) considers various data about the ribosomal proteins in a comprehensive manner to predict disease information, prediction accuracy may be further improved.

So far, the detailed structure and learning method of a prediction model according to the first embodiment of the present disclosure has been described with reference to FIG. 5. In what follows, the detailed structure and learning method of a prediction model according to a second embodiment of the present disclosure will be described with reference to FIG. 6.

Figure 6:
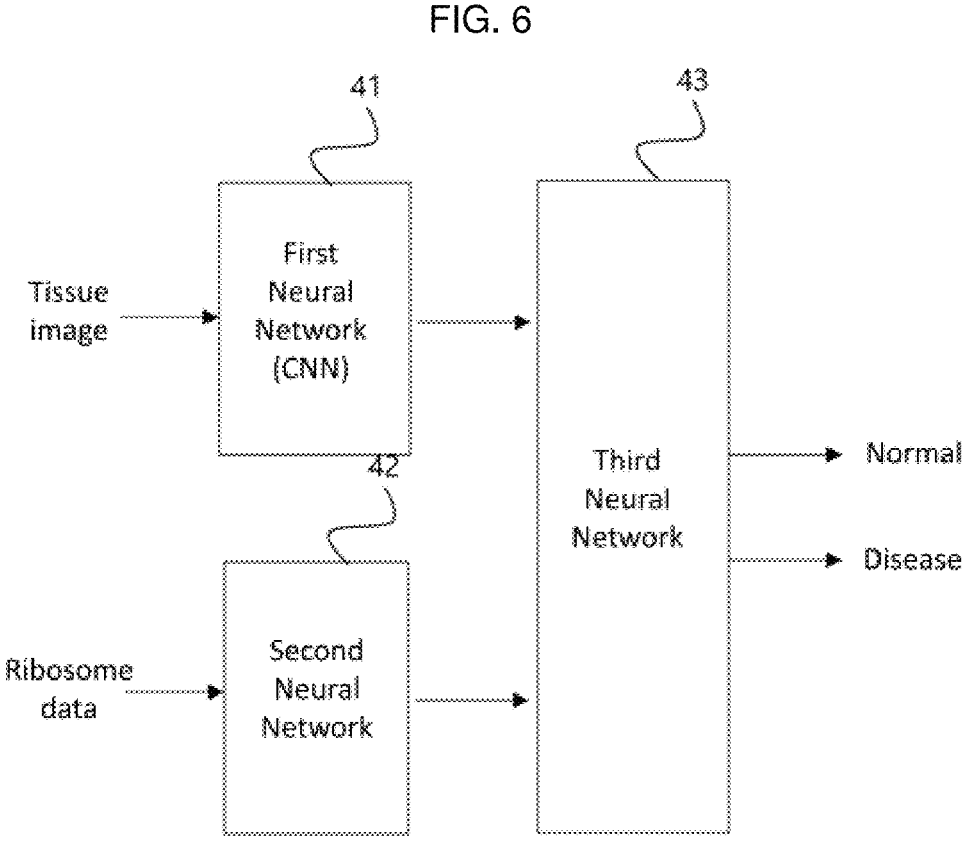
FIG. 6 is an exemplary diagram illustrating the detailed structure and learning method of a disease prediction model according to a second embodiment of the present disclosure.

FIG. 6 is an exemplary diagram illustrating the detailed structure and learning method of a prediction model according to a second embodiment of the present disclosure.

As shown in FIG. 6, the prediction model according to the second embodiment may be configured to include a first neural network 41, a second neural network 42, and a third neural network 43. Also, the prediction model may be configured to provide the outputs of the first neural network 41 and the second neural network 42 to the third neural network 43 as input data.

The first neural network 41 may be trained to output a first output value associated with disease information by receiving a tissue image. The first neural network 41 may be a convolutional neural network specialized for image processing and may be trained to output feature values associated with a disease (e.g., a feature map or an activation map) or lesion information (e.g., lesion location, lesion type, and tumor proliferation score) from the tissue image.

Next, the second neural network 42 may be trained to receive ribosome data and output a second output value associated with the disease information. As mentioned above, the ribosome data may include, for example, various data related to the expression rates of the ribosomal proteins. The second neural network 42 may be, for example, an artificial neural network but is not limited thereto.

Next, the third neural network 43 may be trained to output predictions for disease information using the first output and the second output as inputs. For example, if the third neural network 43 synthesizes the first and second outputs and outputs a prediction value related to the presence or absence of a disease (e.g., a confidence score for each class), training may be performed by backpropagating errors between output prediction values and the ground truth values and updating the weights of the third neural network 43. The weights of the first neural network 41 and/or the second neural network 42 may also be updated by the error backpropagation. The third neural network 43 may be, but is not limited to, an artificial neural network (e.g., a fully connected layer).

In some examples, the first neural network 41 may be pre-trained. Specifically, the first neural network 41 is pre-trained separately to extract features related to disease information from a tissue image, and the first neural network 41 may not be trained when the second neural network 42 and the third neural network 43 are trained. Alternatively, the first neural network 41 may be trained together, and the weights of the first neural network 41 may be fine-tuned. In any case, since the first neural network 41 may be intensively trained in advance to extract features related to disease information accurately, the performance of the prediction model may be improved.

The prediction model trained as described above may predict the disease information on an examinee's target tissue from the examinee's tissue image and ribosome data. For example, the prediction model may receive the examinee's tissue image and ribosome data and output a prediction value regarding the presence or absence of a disease in the target tissue.

So far, the detailed structure and learning method of a prediction model according to the second embodiment of the present disclosure has been described with reference to FIG. 6. According to the method above, since a prediction model is trained to predict disease information by further considering disease-related features appearing in a tissue image, prediction accuracy of the prediction model may be further improved. In what follows, a detailed structure and learning method of a prediction model according to a third embodiment of the present disclosure will be described with reference to FIG. 7.

Figure 7:
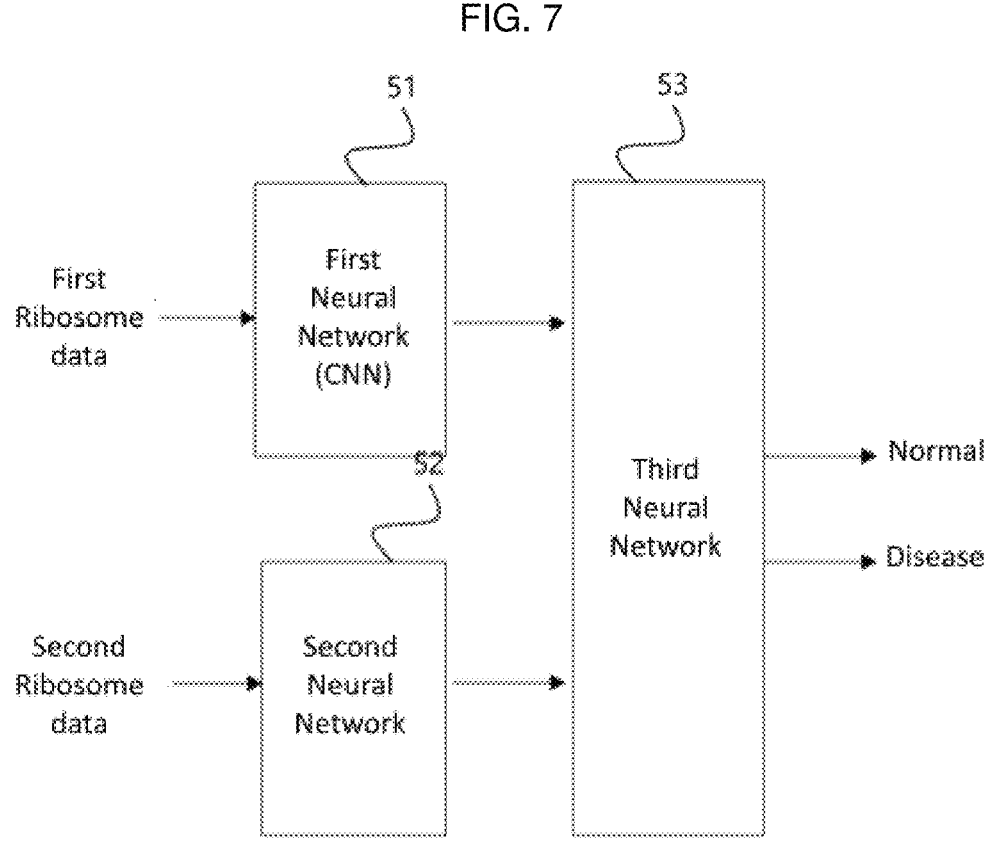

FIG. 7 is an exemplary diagram illustrating the detailed structure and learning method of a disease prediction model according to a third embodiment of the present disclosure.

As shown in FIG. 7, the prediction model according to the third embodiment may be configured to include a first neural network 51, a second neural network 52, and a third neural network 53. Also, the prediction model may be configured to provide the outputs of the first neural network 51 and the second neural network 52 to the third neural network 53 as input data.

The first neural network 51 may be trained to output a first output value associated with disease information by receiving first ribosome data. Here, the first ribosome data may be obtained by processing ribosome-related data in the form of a 2-D (or 3-D) image, and the first neural network 51 may be a convolutional neural network specialized for image processing and may be trained to analyze the first ribosome data through convolutional computations. However, it should be noted that various methods may be employed for generating the first ribosome data.

In some examples, first ribosome data may be generated by processing the expression level or expression rate due to the location of a ribosomal protein (i.e., the expression distribution of ribosomal proteins in a ribosome) into 2-D (or 3-D) data. To provide the convenience of understanding, the present example will be described with reference to FIG. 8.

Figure 8:
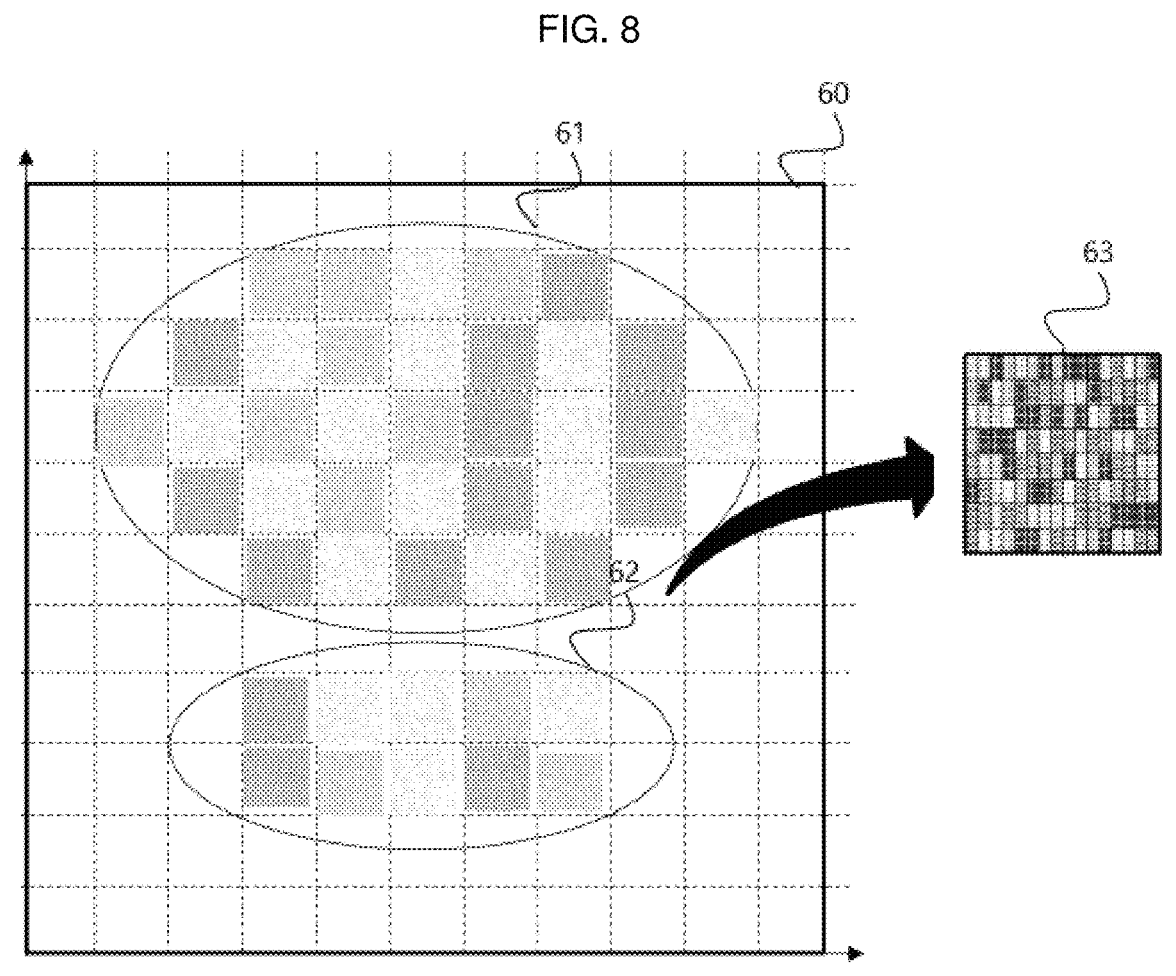

FIG. 8 illustrates a case in which the expression levels due to the locations of ribosomal proteins in the ribosome subunits 61, 62 are processed in the form of a heat map. As illustrated in the figure, a 2-D heat map image 63 (i.e., first ribosome data) may be generated by mapping the ribosome subunits 61, 62 on the 2-D plane 60 and assigning appropriate pixel values according to the protein expression level at the mapped locations. At this time, a particular channel of the heat map image 63 may further include type information of ribosomal proteins expressed at the corresponding location. When the heat map image 63 and disease information are used as training data, the first neural network 51 may learn the relationship between the expression distribution of the ribosomal proteins and the disease information (e.g., the probability of a disease is high when proteins are low-expressed or overexpressed at a particular site of the ribosome). Thus, the prediction accuracy of the prediction model may be further improved.

In some other examples, the first ribosome data may be generated by processing the location relationship (or linkage) between ribosomal proteins into 2-D (or 3-D) data. To provide the convenience of understanding, the present example will be further described with reference to FIG. 9.

Figure 9:
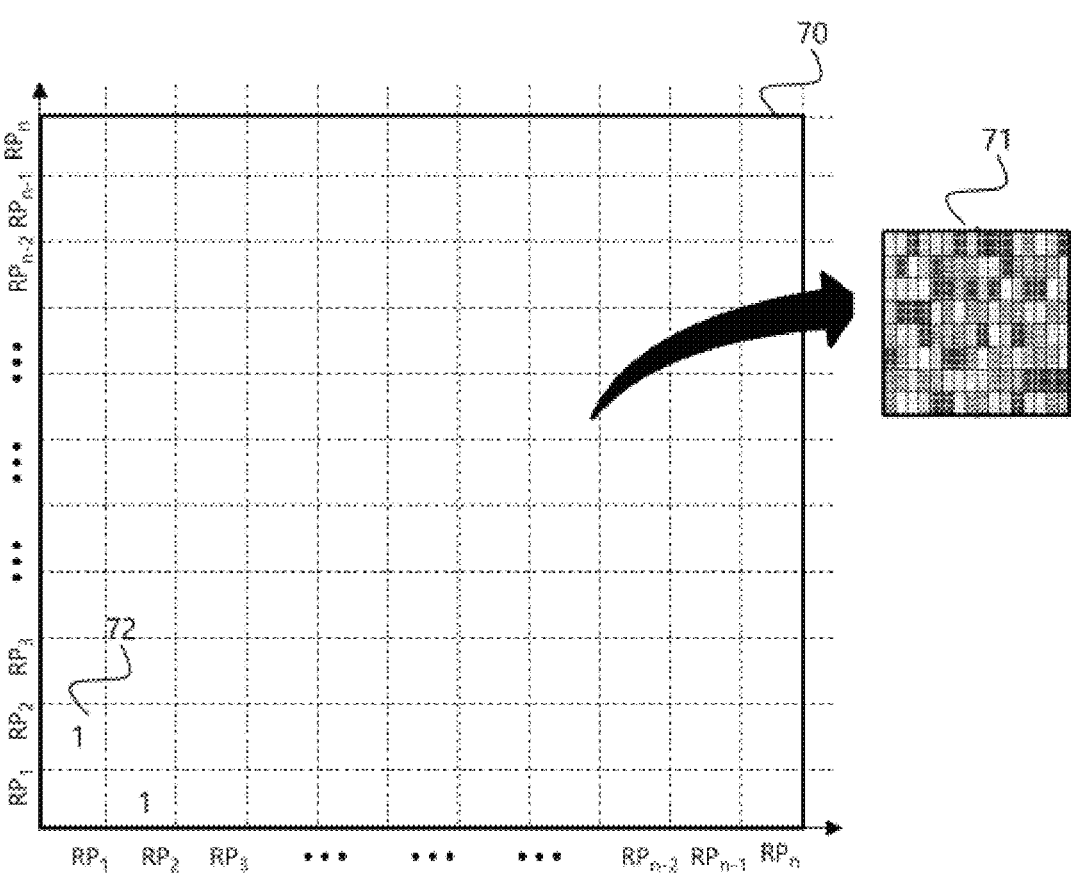

Referring to FIG. 9, a 2-D image 71 (i.e., first ribosome data) may be generated by assigning a value indicating the location relationship of a ribosomal protein pair (e.g., $RP_1$-

RP$_2$) on the 2-D plane (or matrix) 70 formed by two axes corresponding to ribosomal proteins. For example, when a first ribosomal protein (e.g., RP$_1$) and a 2nd ribosomal protein (e.g., RP$_2$) are located close to each other for constructing a ribosome, a predetermined value (e.g., 1) may be assigned to the mapping position 72 of the 2-D plane 70. At this time, a different value may be assigned according to the closeness between the two ribosomal proteins (e.g., the closer the distance, the greater the value). When this image 71 and disease information are used as training data, the first neural network 51 may learn the relationship between the location distribution of ribosomal proteins and the disease information (e.g., the probability of having a disease is high when certain types of ribosomal proteins are clustered together). Thus, the prediction accuracy of the prediction model may be further improved.

By referring again to FIG. 7, descriptions of other neural networks 52, 53 constituting a prediction model will be continued.

The second neural network 52 may be trained to receive second ribosome data and output a second output value associated with disease information. The ribosome data may include, for example, various data related to the expression rates of ribosomal proteins. Also, the second neural network 52 may be, for example, an artificial neural network but is not limited thereto.

Next, the third neural network 53 may be trained to output predictions for disease information using the first output and the second output as inputs. For example, if the third neural network 53 synthesizes the first and second outputs and outputs a prediction value related to the presence or absence of a disease (e.g., a confidence score for each class), training may be performed by backpropagating errors between output prediction values and the ground truth values and updating the weights of the third neural network 53. The weights of the first neural network 51 and/or the second neural network 52 may also be updated by the error backpropagation.

In some examples, the first neural network 51 may be pre-trained. Specifically, the first neural network 51 is pre-trained separately to extract features related to disease information from first ribosome data in the form of an image, and the first neural network 51 may not be trained when the second neural network 52 and the third neural network 53 are trained. Alternatively, the first neural network 51 may be trained together, and the weights of the first neural network 51 may be fine-tuned. In any case, since the first neural network 51 may be intensively trained in advance to extract features related to disease information accurately, the performance of the prediction model may be improved.

The prediction model trained as described above may predict the disease information from the examinee's ribosome data. For example, the prediction model may receive the examinee's first and second ribosome data and output a prediction value regarding the presence or absence of a disease.

So far, the detailed structure and learning method of a prediction model according to the third embodiment of the present disclosure has been described with reference to FIGS. 7 to 9. According to the method above, since a prediction model is trained in such a way to further consider disease-related features appearing in the ribosome data processed in the form of an image, prediction accuracy for disease information may be improved. In what follows, a detailed structure and learning method of a prediction model according to a fourth embodiment of the present disclosure will be described with reference to FIG. 10.

Figure 10:
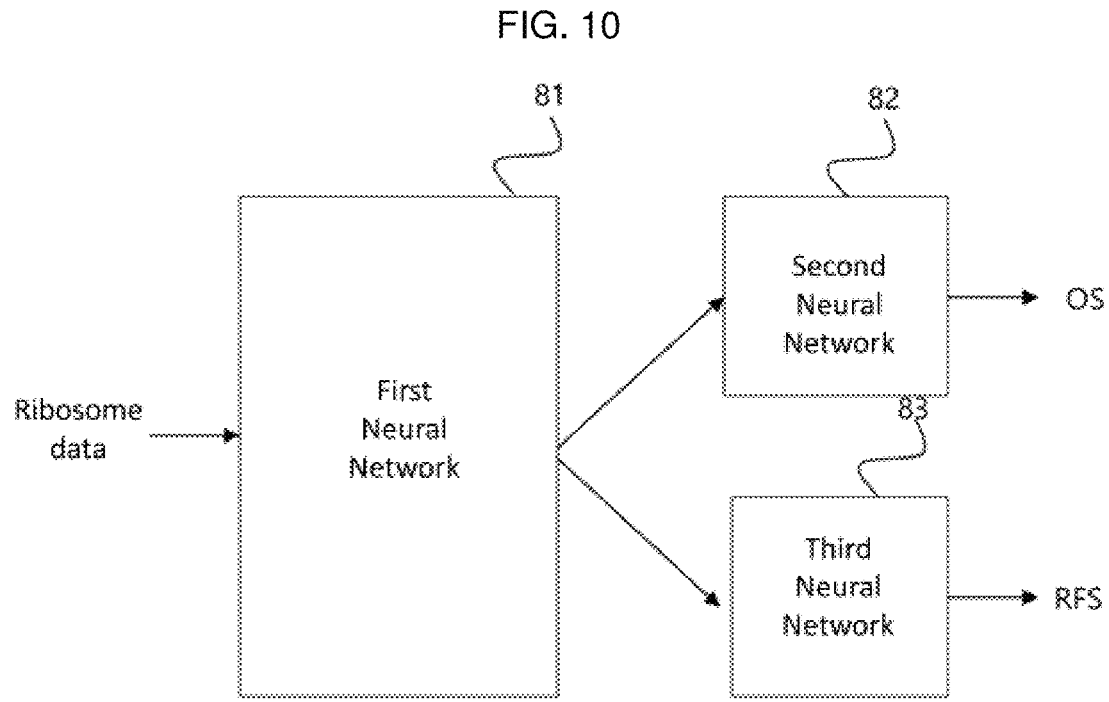
FIG. 10 is an exemplary diagram illustrating the detailed structure and learning method of a disease prediction model according to a fourth embodiment of the present disclosure.

FIG. 10 is an exemplary diagram illustrating the detailed structure and learning method of a disease prediction model according to a fourth embodiment of the present disclosure.

As shown in FIG. 10, a prediction model according to the fourth embodiment may predict prognosis information among disease information, where the prognosis information may include, for example, an overall survival (OS) period and a relapse-free survival (RFS) period but is not limited thereto.

The prediction model according to the fourth embodiment may be configured to include a first neural network 81, a second neural network 82, and a third neural network 83. Also, the prediction model may be configured to provide the outputs of the first neural network 81 to the second neural network 82 and the third neural network 83 as input data.

The first neural network 81 may be trained to output an output value associated with prognosis information by receiving ribosome data. For example, the first neural network 81, which is a kind of shared neural network, may be trained to extract features commonly associated with an overall survival period (or overall survival rate) and a relapse-free survival period (or relapse-free survival rate) from ribosome data entered. The output values of the first neural network 81 may be entered to the second neural network 82 and the third neural network 83. The first neural network 81 may be, for example, an artificial neural network but is not limited thereto.

Next, the second neural network 82 may be trained to receive the output value of the first neural network 81 and output a prediction value of the overall survival period. In some examples, ribosome data input to the first neural network 81 may also be input to the second neural network 82. The second neural network 82 is a neural network specialized in predicting the overall survival period and may be trained to predict the overall survival period based on the output value of the first neural network 81 by considering the features specific to the overall survival period. The second neural network 82 may be, for example, an artificial neural network but is not limited thereto.

Next, the third neural network 83 may be trained to receive the output value of the first neural network 81 and output a prediction value of the relapse-free survival period. In some examples, ribosome data input to the first neural network 81 may also be input to the third neural network 83. The third neural network 83 is a neural network specialized in predicting the relapse-free survival period and may be trained to predict the relapse-free survival period based on the output value of the first neural network 81 by considering the features specific to the relapse-free survival period. The third neural network 83 may be, for example, an artificial neural network but is not limited thereto.

Various methods may be employed to train the prediction model of FIG. 10.

First, the first neural network 81 and the second neural network 82 described above may be trained using ribosome data and information on the overall survival period, and the first neural network 81 and the third neural network 83 may be trained using the ribosome data and the information on the relapse-free survival period. In this case, the first neural network 81 may be trained to extract features commonly associated with the overall survival period and the relapse-free survival period from the ribosome data; and the second neural network 82 and the third neural network 83 may be trained to extract features specific to the overall survival period and features specific to the relapse-free survival period respectively from the ribosome data and to predict the overall survival period and the relapse-free survival period by considering the extracted features and the commonly associated features.

In some examples, training data including ribosome data may be classified based on the difference between the overall survival period and the relapse-free survival period, and the prediction model may be trained using the classified training data. For example, the training data may be classified into first training data in which the difference between the two periods is below a threshold and second training data in which the difference is above the threshold. Also, the first neural network 81 may be trained using the first training data, and the second neural network 82 and the third neural network 83 may be trained using the second training data. In this case, the first neural network 81 may be trained to better extract features of ribosome data commonly associated with the overall survival period and the relapse-free survival period, and the second neural network 82 and third neural network 83 may be trained to better extract features specific to the overall survival period and the relapse-free survival period, respectively. Alternatively, first training may be performed on the entire neural networks 81, 82, 83 with the entire training data, and second training may be performed on the associated neural networks 81, 82, 83 using the first training data and the second training data. The second training may also be performed in the form of weighted learning. For an example of a weighted learning method, refer to the descriptions of FIGS. 11 to 13. Alternatively, the first training may be performed on the associated neural networks 81, 82, 83 using the first and second training data, and the second training may be performed on the entire neural network 81, 82, 83 using the entire training data.

So far, the detailed structure and learning method of a prediction model according to the 4th embodiment of the present disclosure has been described with reference to FIG. 10. According to the method above, by constructing a prediction model based on a neural network that learns the features commonly associated with the overall survival period and the relapse-free survival period and a neural network that learns the features specific to the overall survival period and the relapse-free survival period, training may be performed efficiently, and prediction accuracy for prognosis information may also be improved.

So far, although the first to fourth embodiments of the present disclosure have been described separately with reference to FIGS. 5 to 10, the first to fourth embodiments described above may be combined in various forms. For example, the prediction model may consist of the first neural network receiving a tissue image (e.g., 41 of FIG. 6), the second neural network receiving ribosome data in the form of an image (e.g., 51 of FIG. 7), the third neural network receiving ribosome data (e.g., 42 of FIG. 6 and 52 of FIG. 7), and the fourth neural network (e.g., 43 of FIG. 6 and 53 of FIG. 7) predicting disease information by receiving the output values of the first to third neural networks.

Meanwhile, in some embodiments of the present disclosure, weighted learning may be performed to improve the prediction performance of the disease prediction model. Here, weighted learning may mean training a model with varying training intensity depending on the training data. In this case, the performance of the model may be improved as important training data (e.g., ribosome data samples associated with disease information) are learned more strongly; hereinafter, the present embodiment will be described in detail with reference to FIGS. 11 to 13.

Figure 11:
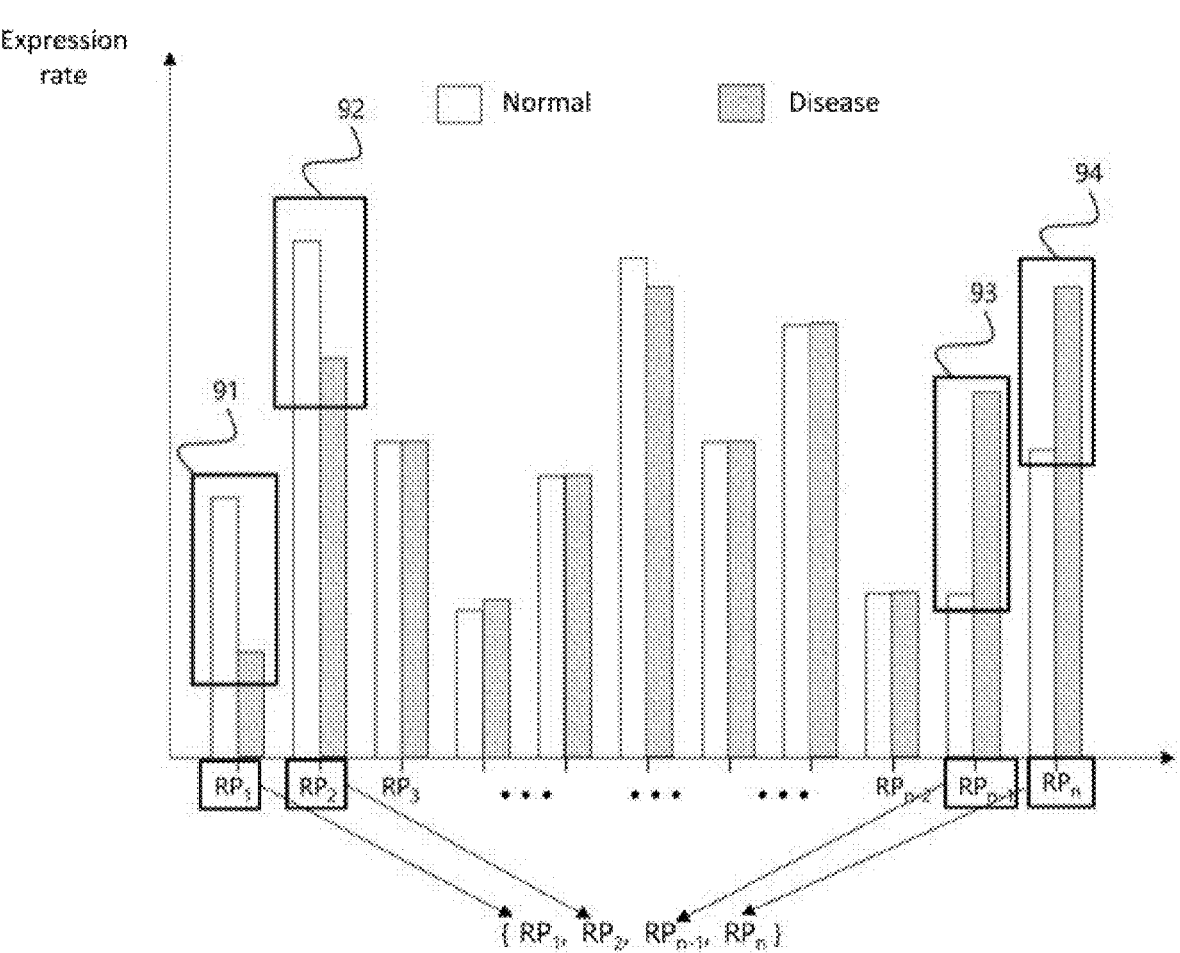
FIG. 11 illustrates a weighted learning method according to a first embodiment of the present disclosure.

FIG. 11 illustrates a weighted learning method according to a first embodiment of the present disclosure.

The weighted learning method according to the first embodiment may start with a step of detecting the expression pattern of ribosomal proteins associated with disease information by analyzing the expression rates of the ribosomal proteins included in training data.

For example, as shown in FIG. 11, the ribosomal protein expression rate of a normal person may be compared with that of a diseased person. The expression patterns (e.g., $\{RP_1, RP_2, RP_{n-1}, RP\}$) may be determined based on the ribosomal proteins ($RP_1$, $RP_2$, $RP_3$, $RP_n$) belonging to the portions (91 to 94) in which the difference of expression rates is greater than or equal to a threshold. Alternatively, the expression patterns (e.g., $\{RP_1, RP_2, RP_3, RP_n\text{-}2\}$) may be determined based on a combination of first ribosomal proteins (e.g., $RP_1$, $RP_2$) for which the difference of expression rates is greater than or equal to the threshold and second ribosomal proteins (e.g., $RP_3$, $RP_{n-2}$) for which the difference is below the threshold. Alternatively, the expression patterns (e.g., $\{RP_1>0.5$ and $RP_3<0.2\}$) may be determined based on various combinations of types of ribosomal proteins and expression rate conditions.

As another example, an expression pattern associated with a disease (e.g., ribosomal proteins that appear in a large number of diseased persons and whose expression rate is above or below a threshold) may be detected by analyzing the ribosomal protein expression rate of a diseased person, and a normal expression pattern (e.g., ribosomal proteins that appear in a large number of normal persons and whose expression rate is above or below a threshold) may be detected by analyzing the ribosomal protein expression rate of a normal person.

In the next step, a sample weight may be assigned to each data sample that makes up training data using the detected expression pattern. For example, sample weights may be given differently according to the similarity between the detected expression pattern and the data sample. More specifically, a first data sample that fully conforms to the detected expression pattern (or a data sample including the expression pattern) may be given the highest sample weight, and a second data sample that partially conforms to the detected expression pattern may be given a lower sample weight than the first data sample. Similarly, a third data sample that does not conform to the detected expression pattern may be given the lowest sample weight.

In the next step, a prediction model may be trained based on the sample weights given. In other words, the prediction model may be trained more strongly for those data samples with high sample weights. However, specific learning methods may vary.

In some examples, before updating the weights of the prediction model based on the prediction error for a data sample (i.e., the difference between a predicted value and the ground-truth value), the error may be increased or decreased based on the sample weight. For example, the higher the sample weight, the greater the error, and vice versa. Also, the weights of the prediction model may be updated based on increased or decreased error values. In this case, since error related to the data sample with a high sample weight is expected to have a greater influence on the prediction model, weighted learning according to the sample weights may be effectively performed.

In some other examples, the number of trainings for data samples may vary based on the sample weights. For example, further training may be performed for those data samples with a high sample weight.

In some other examples, when a data sample is entered into a prediction model, the value of the data sample (e.g., the expression rate value of a ribosomal protein) may be increased or decreased based on the sample weight. For example, as a sample weight becomes higher, the corresponding data sample has a further increased value, but the data sample value is decreased otherwise. In this case, since a data sample with a high sample weight has a greater influence on the training of the prediction model, weighted learning based on sample weights may be effectively performed.

In some other examples, the training order of data samples may vary based on the sample weights. For example, a data sample with a higher sample weight may be applied for training before data samples with a lower sample weight. Typically, this is because a data sample applied first for training may have a greater influence on the training of a prediction model than those data samples applied later for training.

In some other examples, the prediction model may be trained based on a combination of the preceding examples.

Meanwhile, in some examples, the training data may include information on the progression stage of a disease (e.g., early, middle, late, 1st, 2nd, and 3rd stage). In addition, when detecting an expression pattern of ribosomal proteins associated with disease information, the ribosomal protein expression rate of a normal person may be compared with the ribosomal protein expression rate of a diseased person in the early stage of disease. In this case, since the sample weights will be given based on the expression patterns appearing in a diseased person at an early stage of the disease, the prediction model may be trained to detect the disease in its early stage better.

So far, a weighted learning method according to the first embodiment of the present disclosure has been described with reference to FIG. 11. In what follows, a weighted learning method according to a second embodiment of the present disclosure will be described with reference to FIGS. 12 and 13.

Figure 12:
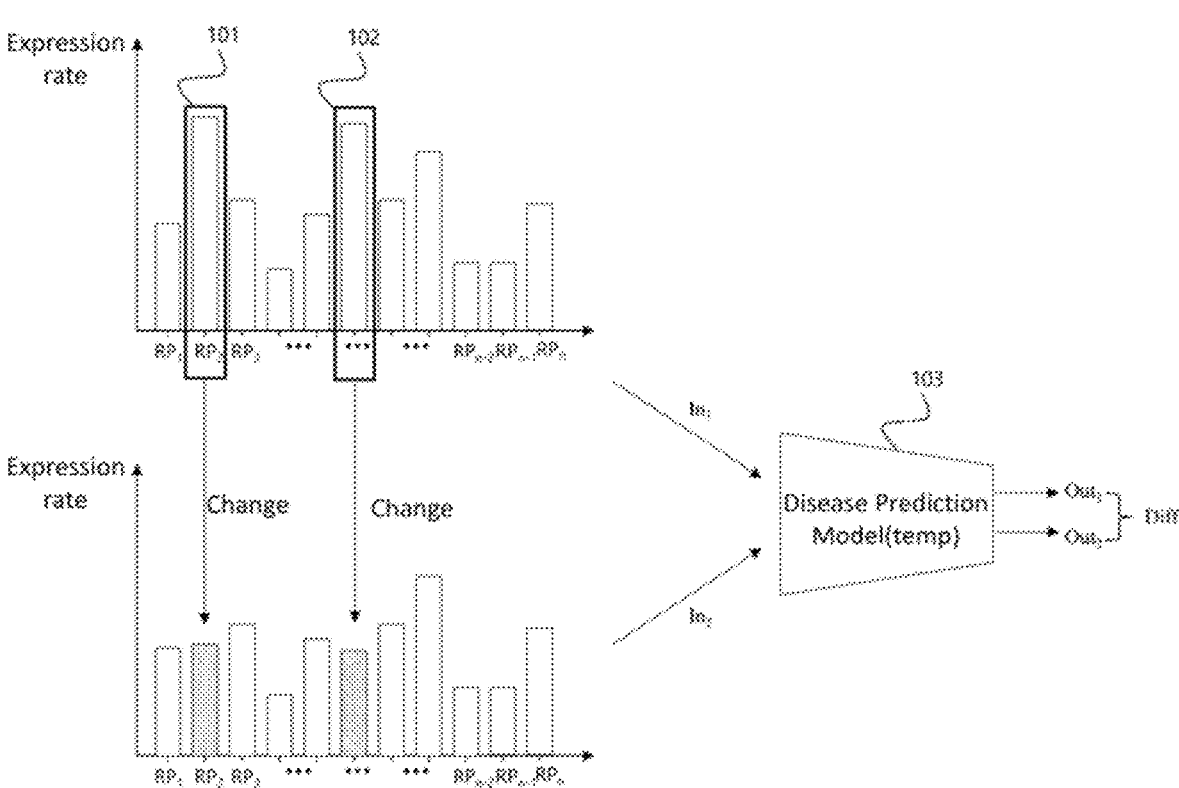
FIGS. 12 and 13 illustrate a weighted learning method according to a second embodiment of the present disclosure.
Figure 13:
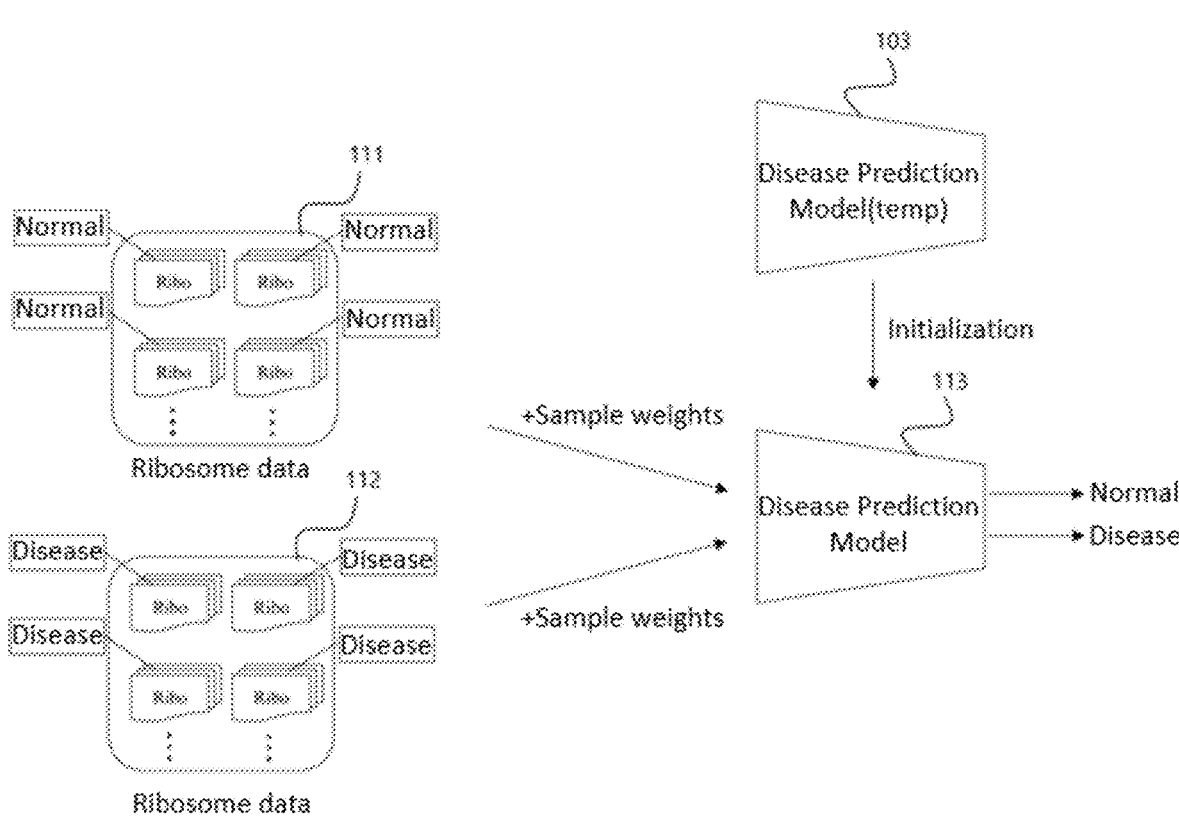

FIGS. 12 and 13 illustrate a weighted learning method according to a second embodiment of the present disclosure. In what follows, descriptions thereof will be given with reference to FIGS. 12 and 13.

The weighted learning method according to the second embodiment may begin with the step of learning training data and constructing a temporary prediction model 103. The structure and learning method of the temporary prediction model 103 may use any suitable approach.

In the next step, at least a portion of expression rates of ribosomal proteins may be changed among first data samples (i.e., samples of ribosomal data) constituting training data to produce second data samples. For example, as shown in FIG. 12, the expression rates of ribosomal proteins 101, 102 whose expression rate is above a threshold may be changed. However, the specifics of the present step may vary.

In some examples, the expression rates of ribosomal proteins in the first data samples, whose expression rate is above (or below) the threshold, may be changed.

In some other examples, the expression rates of the ribosomal proteins randomly selected in the first data samples may be changed. At this time, the number of ribosomal proteins selected may be one or more.

In some other examples, the expression rate of specific ribosomal proteins in the first data samples may be changed to a particular value to produce second data samples. At this time, the particular value may be 0 or an average expression rate of a normal or diseased person. For example, when the first data samples originate from a normal person, the expression rate of the specific ribosomal proteins may be changed to the average expression rate of a diseased person. In the opposite case, the expression rates may be changed to the average expression rate of a normal person.

In some other examples, the second data samples may be generated based on a combination of the preceding examples.

In the next step, a first prediction value (Out$_1$) may be obtained by entering the first data samples into the temporary prediction model 103, and a second prediction value (Out$_2$) may be obtained by entering the second data samples into the temporary prediction model 103. Then, a difference (Diff) between the two prediction values may be calculated.

In the next step, an expression pattern of ribosomal proteins associated with disease information may be detected based on the difference (Diff) between the two prediction values. For example, if the difference is above a threshold, the expression pattern may be determined based on the ribosomal proteins 101, 102 in the first data samples whose expression rates have been changed. This is because a significant change of a prediction value in the temporary prediction model due to the change of the expression rate of specific ribosomal proteins 101, 102 means that the expression rate of the specific ribosomal proteins 101, 102 has a significant influence on the prediction of disease information (i.e., acts as a key feature). For a specific method for determining the expression pattern, the descriptions given with reference to FIG. 11 should be referenced.

In the next step, sample weights may be assigned to each data sample constituting the training data 111, 112 using the detected expression pattern. In this regard, the descriptions of FIG. 11 should be further referenced.

In the next step, the prediction model 113 may be constructed by re-learning the training data 111, 112 based on the sample weights assigned. For example, the prediction model 113 at the initialized state (i.e., a state in which the weights of the model are set to their initial values) may be retrained based on the sample weights. In this regard, the descriptions of FIG. 11 should be further referenced.

So far, the weighted learning method according to some embodiments of the present disclosure has been described with reference to FIGS. 11 to 13. According to the method above, weighted learning may be performed on data samples presumed to be highly associated with disease information. Accordingly, training of a prediction model may be performed more effectively, and the prediction performance thereof may also be greatly improved.

In what follows, a computing device 120 capable of implementing the prediction device 10 according to some embodiments of the present disclosure will be described.

Figure 14:
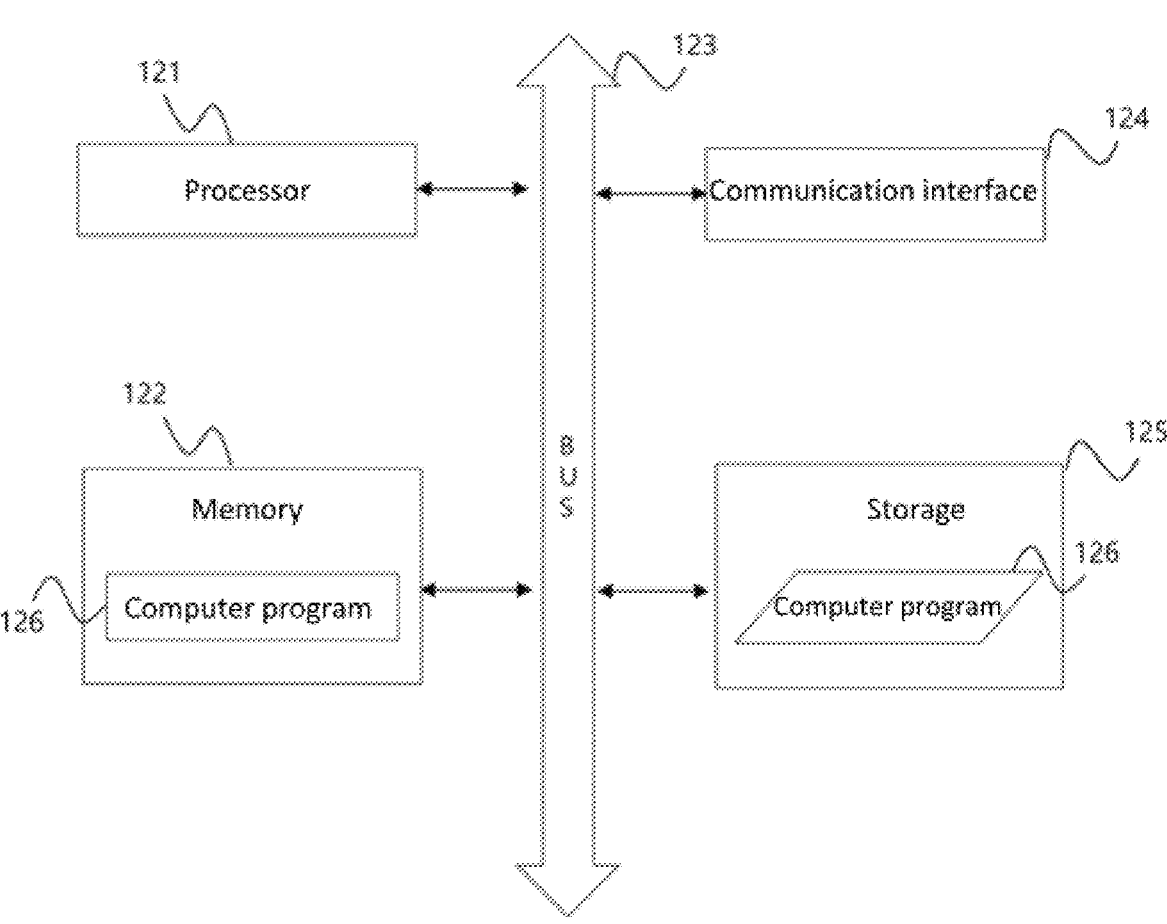
FIG. 14 illustrates a computing device capable of implementing an apparatus for predicting disease according to some embodiments of the present disclosure.

FIG. 14 illustrates a hardware structure of the computing device 120.

As shown in FIG. 14, the computing device 120 may comprise one or more processors 121, a bus 123, a communication interface 124, a memory 122 that loads a computer program performed by the processor 121, and a storage 125 that stores the computer programs 126. However, FIG. 14 shows only those constituting elements related to the embodiment of the present disclosure. Accordingly, it should be understood by those skilled in the art to which the present disclosure belongs that other general-purpose constituting elements may be further included in addition to the constituting elements shown in FIG. 14. In other words, the computing device 120 may further include various constituting elements in addition to the constituting elements shown in FIG. 14. Alternatively, the computing device 120 may be composed by excluding some of the constituting elements shown in FIG. 14.

The processor 121 may control the overall operation of each configuration of the computing device 120. The processor 121 may be configured by including at least one of a Central Processing Unit (CPU), a Micro-Processor Unit (MPU), a Micro-Controller Unit (MCU), a Graphics Processing Unit (GPU), or any arbitrary type of processor well known to the technical field of the present disclosure. Also, the processor 121 may perform operations on at least one application or program for executing the methods/operations according to embodiments of the present disclosure. The computing device 120 may be equipped with one or more processors.

The memory 122 may store various data, instructions, and/or information. The memory 122 may load one or more computer programs 126 from the storage 125 to execute the methods/operations according to the embodiments of the present disclosure. The memory 122 may be implemented using a volatile memory such as RAM but is not limited thereto.

The bus 123 may provide a communication function between the constituting elements of the computing device 120. The bus 123 may be implemented using various types of buses such as address bus, data bus, and control bus.

The communication interface 124 may support wired and wireless Internet communication of the computing device 120. In addition, the communication interface 124 may support various communication schemes in addition to Internet communication. To this end, the communication interface 124 may be configured to include a communication module well known in the technical field of the present disclosure.

The storage 125 may store the one or more programs 126 non-temporarily. The storage 125 may be configured to include non-volatile memory such as a Read-Only Memory (ROM), an Erasable Programmable ROM (EPROM), an Electrically Erasable Programmable ROM (EEPROM), and a flash memory; a hard disk; a removable disk; or any type of computer-readable recording medium well known in the technical field to which the present disclosure belongs.

The computer program 126, when loaded into the memory 122, may include one or more instructions that instruct the processor 121 to perform the methods/operations according to various embodiments of the present disclosure. In other words, by executing the one or more instructions, the processor 121 may perform the methods/operations according to various embodiments of the present disclosure.

For example, the computer program 126 may include one or more instructions that instruct the processor to perform an operation of constructing a disease prediction model by learning ribosome data for training and training data including disease information, an operation of acquiring ribosome test data of an examinee, and an operation of predicting disease information of the examinee from the ribosome test data by using the disease prediction model. In this case, the prediction device 10 according to some embodiments of the present disclosure may be implemented through the computing device 120.

The technical principles and spirit of the present disclosure, described so far with reference to FIGS. 1 to 14, may be implemented in computer-readable code on a computer-readable medium. The computer-readable recording medium may include, for example, a removable recording medium (CD, DVD, Blu-ray Disc, USB storage device, removable hard disk), or a stationary recording medium (ROM, RAM, or a built-in computer hard disk). The computer program recorded in a computer-readable recording medium may be transmitted to a different computing device through a network such as the Internet and installed in the different computing device, thereby being used in the different computing device.

In the above, just because all the constituting elements comprising an embodiment of the present disclosure are combined into one or operate in combination with each other does not mean that the technical principles and spirit of the present disclosure are necessarily limited to the embodiment. In other words, as long as being within the technical scope of the present disclosure, all the constituting elements may operate by being selectively integrated into one or more combinations.

Although the operations are shown in a particular order in the figure, it should not be understood that the operations have to be performed in that order or in the sequential order according to which the operations are shown or that a desired result may be achieved only when all the illustrated operations are executed. In certain situations, multitasking and parallel processing may be advantageous. Moreover, separation into various configurations in the embodiments described above should not be understood as being required necessarily, and the program components and systems described above may generally be integrated into a single software product or packaged into multiple software products.

So far, although the embodiments of the present disclosure have been described with reference to appended drawings, it should be understood by those skilled in the art to which the present disclosure belongs that the present disclosure may be embodied in other specific forms without changing the technical principles or essential characteristics of the present disclosure. Therefore, the embodiments described above should be regarded as being illustrative rather than restrictive in every aspect. The technical scope of the present disclosure should be determined by the appended claims given below, and it should be understood that all of the technical principles found within the range equivalent to the technical scope of the present disclosure should be interpreted to belong thereto.

What is claimed is:

1. A method for predicting disease of an examinee in a computing device, the method comprising:

constructing a disease prediction model by learning ribosome data for training and training data including disease information;

acquiring ribosome test data of the examinee; and predicting disease information of the examinee from the ribosome test data by using the disease prediction model, wherein the ribosome data for training and the ribosome test data include data related to expression rates of ribosomal proteins, wherein constructing the disease prediction model comprises:

constructing a temporary disease prediction model by learning the training data;

generating second ribosome data samples by changing at least part of expression rates of ribosomal proteins in first ribosome data samples constituting the ribosome data for training;

acquiring a first prediction value by entering the first ribosome data samples into the temporary disease prediction model and acquiring a second prediction value by entering the second ribosome data samples into the temporary disease prediction model;

detecting an expression pattern of ribosomal proteins associated with the disease information based on a difference between the first prediction value and the second prediction value;

assigning sample weights to data samples constituting the training data using the detected expression pattern; and constructing the disease prediction model by re-learning the training data based on the sample weights, wherein the training data are stored in a memory of the computing device, and wherein constructing the disease prediction model is executed by a processor of the computing device performing numerical operations on the training data stored in the memory.

2. The method of claim 1, wherein the ribosome data for training further include protein expression rates between a large sub-unit and a small sub-unit and data on ribosomal proteins with an expression level above a threshold and ribosomal proteins with an expression level below the threshold.

3. The method of claim 1, wherein the training data further include an image of a target tissue, and the disease prediction model includes:

a first neural network receiving the image of the target tissue and outputting a first output value related to the disease information, a second neural network receiving the ribosome data for training and outputting a second output value related to the disease information, and a third neural network predicting disease information on the target tissue by receiving the first output value and the second output value, wherein the first neural network is composed of convolutional neural networks.

4. The method of claim 1, wherein the disease prediction model includes:

a first neural network receiving data in the form of an image related to the ribosomal proteins and outputting a first output value related to the disease information, a second neural network receiving the ribosome data for training and outputting a second output value related to the disease information, and a third neural network predicting disease information by receiving the first output value and the second output value, wherein the first neural network is composed of convolutional neural networks.

5. The method of claim 4, wherein the data in the form of an image represent expression levels or expression rates due to locations of ribosomal proteins in a ribosome.

6. The method of claim 4, wherein the data in the form of an image is generated by assigning values due to location relationships of ribosomal protein pairs onto a 2-D plane formed by two axes corresponding to ribosomal proteins.

7. The method of claim 1, wherein the disease information includes information on an overall survival period and a relapse-free survival period of a diseased person;

the disease prediction model includes:

a first neural network receiving the ribosome data for training and outputting an output value related to the disease information, a second neural network receiving the output value and predicting the overall survival period, and a third neural network predicting the relapse-free survival period by receiving the output value; and the constructing the disease prediction model includes:

training the first neural network and the second neural network using the ribosome data for training and the information on the overall survival period and training the first neural network and the third neural network using the ribosome data for training and the information on the relapse-free survival period.

8. The method of claim 7, wherein the training the first neural network and the second neural network includes:

classifying the training data into first training data in which a difference between the overall survival period and the relapse-free survival period is below a threshold and second training data in which the difference is above the threshold;

training the first neural network using the first training data; and training the second neural network using the second training data.

9. The method of claim 1, wherein the constructing the disease prediction model includes detecting an expression pattern of ribosomal proteins associated with the disease information by comparing a ribosomal protein expression rate of a normal person with a ribosomal protein expression rate of a diseased person;

assigning sample weights to data samples constituting the training data using the detected expression pattern; and learning the training data based on the sample weights.

10. The method of claim 9, wherein the disease information further includes information on a progression stage of disease, and the detecting an expression pattern of the ribosomal proteins includes comparing the ribosomal protein expression rate of a normal person with the ribosomal protein expression rate of a diseased person at an early stage of disease.

11. An apparatus for predicting disease, the apparatus comprising:

a memory storing one or more instructions; and a processor configured to perform, by executing the stored one or more instructions, an operation of constructing a disease prediction model by learning ribosome data for training and training data including disease information, an operation of acquiring ribosome test data of an examinee, and an operation of predicting disease information of the examinee from the ribosome test data using the disease prediction model, wherein the ribosome data for training and the ribosome test data include data related to expression rates of ribosomal proteins, wherein constructing the disease prediction model comprises:

constructing a temporary disease prediction model by learning the training data;

generating second ribosome data samples by changing at least part of expression rates of ribosomal proteins in first ribosome data samples constituting the ribosome data for training;

acquiring a first prediction value by entering the first ribosome data samples into the temporary disease prediction model and acquiring a second prediction value by entering the second ribosome data samples into the temporary disease prediction model;

detecting an expression pattern of ribosomal proteins associated with the disease information based on a difference between the first prediction value and the second prediction value;

assigning sample weights to data samples constituting the training data using the detected expression pattern; and constructing the disease prediction model by re-learning the training data based on the sample weights, wherein the training data are stored in a memory of the computing device, and wherein constructing the disease prediction model is executed by a processor of the computing device performing numerical operations on the training data stored in the memory.

12. A computer program stored in a computer-readable recording medium, the computer program, being combined with a computing device, comprising:

constructing a disease prediction model by learning ribosome data for training and training data including disease information;

acquiring ribosome test data of an examinee; and predicting disease information of the examinee from the ribosome test data using the disease prediction model, wherein the ribosome data for training and the ribosome test data include data related to expression rates of ribosomal proteins, wherein constructing the disease prediction model comprises:

constructing a temporary disease prediction model by learning the training data;

generating second ribosome data samples by changing at least part of expression rates of ribosomal proteins in first ribosome data samples constituting the ribosome data for training;

acquiring a first prediction value by entering the first ribosome data samples into the temporary disease prediction model and acquiring a second prediction value by entering the second ribosome data samples into the temporary disease prediction model;

detecting an expression pattern of ribosomal proteins associated with the disease information based on a difference between the first prediction value and the second prediction value;

assigning sample weights to data samples constituting the training data using the detected expression pattern; and constructing the disease prediction model by re-learning the training data based on the sample weights, wherein the training data are stored in a memory of the computing device, and wherein constructing the disease prediction model is executed by a processor of the computing device performing numerical operations on the training data stored in the memory.

* * * * *